United States Patent

Gutierrez et al.

[11] Patent Number: 5,488,146
[45] Date of Patent: Jan. 30, 1996

[54] PROCESS FOR THE PREPARATION OF SULFO CARBOXYMETHYLOXYSUCCINIC ACID AND ITS SALTS

[75] Inventors: Eddie N. Gutierrez, Midland Park; Shang-Ren Wu, Mahwah, both of N.J.

[73] Assignee: Lever Brothers Company, Division of Conopco, Inc., New York, N.Y.

[21] Appl. No.: 362,357

[22] Filed: Dec. 22, 1994

[51] Int. Cl.⁶ .................................................... C07C 303/32
[52] U.S. Cl. .......................... 562/109; 562/110; 562/111
[58] Field of Search .................................... 562/109, 110, 562/111

[56] References Cited

U.S. PATENT DOCUMENTS 3,128,287 4/1964 Berg.
3,151,084 9/1964 Schlitz et al..
3,692,685 9/1972 Lamberti et al..
3,920,564 11/1975 Grecsek.
3,925,375 12/1975 Lamberti.
3,957,775 5/1976 Lamberti.
4,397,776 8/1983 Ward.
4,560,491 12/1985 Sherman.
4,663,071 5/1987 Bush et al..
4,704,233 11/1987 Hartman et al..
5,068,420 11/1991 Kreczmer.
5,254,281 10/1993 Pichardo et al..
5,296,588 3/1994 Au et al..
5,336,765 8/1994 Au et al..

*Primary Examiner*—José G. Dees
*Assistant Examiner*—Joseph M. Conrad, III
*Attorney, Agent, or Firm*—James J. Farrell

[57] ABSTRACT

A process for the preparation of SCMOS from sulfur trioxide, maleic anhydride, glycolic acid, and alkaline earth metal hydroxide or mixtures of alkaline earth metal and alkali metal hydroxides is disclosed which cooperatively control pH, temperature, time and ratio of reactants.

8 Claims, No Drawings

PROCESS FOR THE PREPARATION OF SULFO CARBOXYMETHYLOXYSUCCINIC ACID AND ITS SALTS

BACKGROUND OF THE INVENTION

FIELD OF THE INVENTION

The invention relates to the preparation of sulfo carboxymethyloxysuccinic acid (SCMOS) and its salts by a process which produces the compound in reasonable time, temperature and yields. Sulfo carboxymethyloxy succinic acid and its salts are effective sequestering agents and are useful as builders in detergent compositions for household, institutional and industrial use.

RELATED ART

Sulfo carboxymethyloxy succinic acid (SCMOS) and salts thereof are known and are known to have utility as sequestering agents and detergent builders. A disadvantage of SCMOS and salts thereof as detergent builders is that they may be relatively expensive to prepare.

Ether polycarboxylates with more than three proximal carboxylate groups (X) are in general strong binders, e.g., oxydisuccinate (ODS) as disclosed in U.S. Pat. No. 3,128,287 and tartrate monosuccinate (TMS), as disclosed in U.S. Pat. No. 4,663,071.

```
CH2CHOCHCH2        CH2CHOCHCHOH
 |   |   |   |         |   |   |   |
 X   X   X   X         X   X   X   X

ODS                    TMS
```

Those with less than four carboxylate groups are generally weaker builders, having a Log $K_{Ca}$ of about 4.4 or less, e.g., carboxy methyloxy succinate (CMOS) disclosed in U.S. Pat. No. 3,692,685 and citrate.

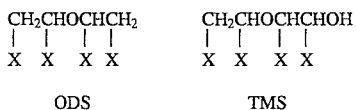

```
                         OH
                         |
CH2CHOCH2           CH2CCH2
 |   |   |           |   | |
 X   X   X           X   XX

CMOS              CITRATE
```

This difference of about 1.3 log $K_{Ca}$ units between the tricarboxylates and the tetracarboxylate warrants the use of the latter as replacements for phosphates in detergent formulations.

The increase in builder efficiency, however, results in a higher cost for the α-hydroxy acids and an increase in stereoisomers which are produced when stereoisomeric hydroxy acids such as malic or tartaric are used. α-hydroxy acids are typically expensive for a mixture of R,S isomers. Reducing the amount of stereoisomers requires the use of pure R or S hydroxy acids. This leads to a dramatic increase in cost, since processes for generating these acids (e.g., malic or tartaric) are usually enzymic in nature.

A way to avoid this problem is to replace any of the carboxylate groups by other anionic groups which are relatively inexpensive but still capable of chelating alkaline earth metals, such as calcium. One such group is sulfonate which is derived from inexpensive sulfur trioxide. Reacting $SO_3$ with maleic anhydride, an inexpensive commodity chemical, produces sulfomaleic anhydride (SMA) a very reactive electrophilic reagent which can be used as an acceptor in a Michael reaction.

Sulfo carboxymethyl succinate (SCMOS) disclosed in U.S. Pat. No. 3,957,775 is a builder produced by reacting sulfo maleic anhydride with an excess of glycolic acid esters. It is theorized that the anhydride is first attacked by the hydroxy group of the glycolate ester to form a mixture of mono esters of sulfo maleic acid. These in turn can add glycolate ester to the double bond either before or after esterification of the free carboxy group by another molecule of glycolate ester as follows:

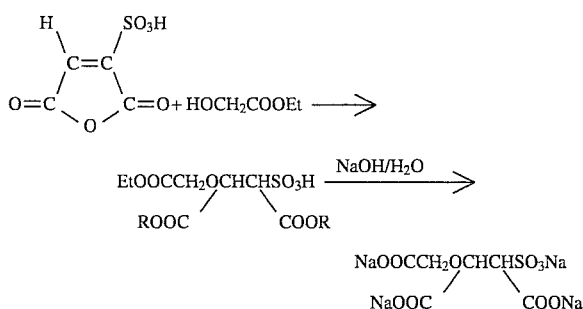

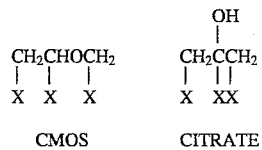

The process has several drawbacks, however. First, four diastereomers will be produced during the acidic Michael conditions and second, the process gives esters of SCMOS which must then be subsequently hydrolyzed to yield the tetrasodium salt. There is no mention of diastereoisomeric products much less that four diastereomers will be produced. There is no mention of calcium binding properties in the patent. Nor is there any mention that SCMOS may be produced under aqueous Michael conditions. There is mention of the conversion of sulfo maleate to sulfo malate using calcium hydroxide, but no details as to the number of diastereomers are given.

It is thus seen as desirable to be able to produce selective isomers of SCMOS in good yield.

A workable and cost-efficient production of SCMOS and its salts must be directed towards optimizing the process conditions in such a manner that selected isomers in reasonable yields are obtained.

Accordingly, it is an object of the present invention to provide a process which produces selective isomers of SCMOS and their salts.

This and other objects and advantages will appear as the description proceeds.

SUMMARY OF THE INVENTION

The attainment of the above objects is made possible by this invention which includes a preparation of SCMOS by a process which includes:

Reaction of sulfur trioxide with maleic anhydride at a mole ratio of the sulfur trioxide to maleic anhydride of about 1.1:1 to 1.3:1 and a temperature of 60° C. to 80° C. to form the sulfo maleic anhydride.

Addition of water and ice to the sulfo maleate and reduction of the pH to about 1 at a temperature of 25° C. to 30° C. and the absence of calcium to retain the double bond and to form the sulfo maleic acid.

Addition of glycolic acid to the sulfo maleic acid together with alkaline earth metal hydroxide or mixtures of alkaline earth metal and alkali metal hydroxides to pH 11 at a temperature of 25° C. to 50° C. and preferably 25° C. to 35° C. with agitation.

Over a period of 1 to 2 hours the pH drops to about 10.2 to 10.5 and the sulfo carboxymethyloxy calcium salt calcium SCMOS precipitates out as it is formed.

The calcium SCMOS may then be converted to the sodium salt by mixing with sodium carbonate or an appropriate ion exchange resin such as Amberlite® IR 120 from Rohm & Haas. The carbonate method preserves the selectivity of the isomers. The ion exchange resin method allows epimerization.

The carbonate process produces a good yield of R,S and S,R isomers of the calcium SCMOS or calcium α-carboxymethyloxy β-sulfosuccinate.

It has been found that the calcium or mixtures of calcium/sodium salts of glycolic acid can add to the salts of sulfo maleate to afford SCMOS in high yield and purity. The reaction requires at least some alkaline earth metal to be present, however, no reaction occurs when sodium hydroxide is the only base.

DETAILED DESCRIPTION OF THE INVENTION

Synthesis of Sulfosuccinates:

Sulfur trioxide reacts with maleic anhydride to afford sulfo maleic anhydride (SMA) according to the following reaction scheme:

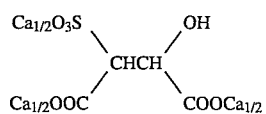

(SMA)

Because of the presence of the sulfonic acid group, sulfomaleic anhydride (SMA) is a much more reactive electrophile than maleic anhydride and will therefore react rapidly with nucleophiles under aqueous Michael conditions. Primary α-hydroxy acids (either in the form of the calcium or calcium/sodium salts) are rapidly added to the salts of sulfo maleate to form ether polycarboxylates as shown below:

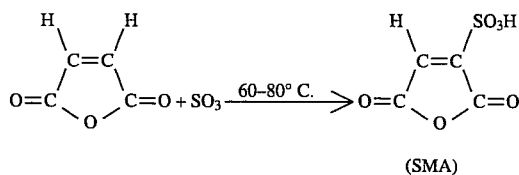

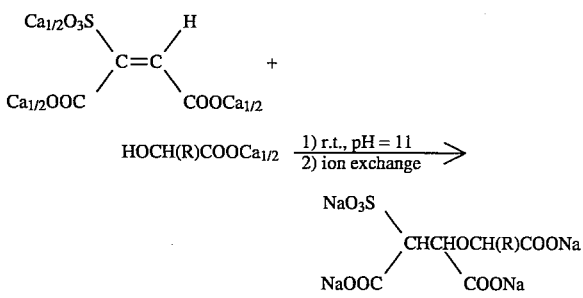

When R is $CH_2COOM$ or $CH_3$, the reaction is quite sluggish and only traces of the desired tetracarboxylate is formed, the bulk of the product being (RS, SR) sulfomalate, formed from the hydration of sulfo maleate as shown below:

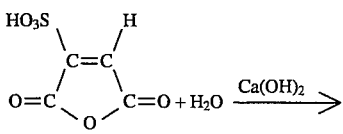

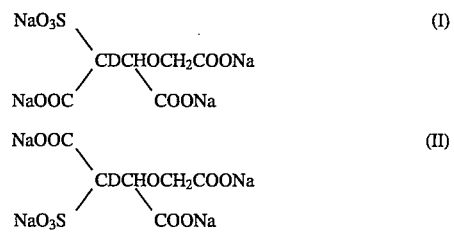

Very little of the (SS, RR) isomers of sulfo malic are formed in this reaction. On the other hand, if the reaction is run under acidic conditions, a 1:1:1:1 mixture of RS:SR:RR:SS sulfo malic is produced.

The addition of glycolate to sulfo maleate also produces a pair of enantiomers (RS, SR) and is most probably stereospecific. In order to generate the pure RR,SS isomer, sulfo fumarate is required as the starting material. However, attempts to prepare this intermediate by either sulfonating fumaric acid or fumaryl chloride are unsuccessful and give, respectively, maleic anhydride or maleyl chloride.

Epimerization of Sulfo CMOS

Sulfo CMOS possesses two asymmetric carbon atoms. The one adjacent to the sulfo group is also flanked by a carboxy group which makes the attached proton acidic and therefore, easily removed. Under acidic conditions, a mixture of RS, SR sulfo CMOS is converted into a mixture of RS, SR, RR,SS. Given a sufficient amount of time, the mixture is converted into a 50:50 mixture of each of a pair of stereoisomers.

That epimerization does occur via this route is evidenced by the deuterium exchange of RS, SR sulfo CMOS in $D_2O/DCl$, to produce a mixture of deuterated diastereomers (I) and (II):

$$NaO_3S\diagdown\atop\diagup CDCHOCH_2COONa \atop NaOOC\diagup\diagdown COONa \quad (I)$$

$$NaOOC\diagdown\atop\diagup CDCHOCH_2COONa \atop NaO_3S\diagup\diagdown COONa \quad (II)$$

$^1H$ NMR shows the CH adjacent to $OCH_2$ as a doublet about 3.9 ppm. This doublet gradually collapses to a singlet (4.3 in this spectrum) and a second singlet at 4.4 ppm corresponding to the other diastereomer. The disappearance of the CH adjacent to the sulfonate group and the presence of just $OCH_2$ groups is also quite evident at 3.9–4.2 ppm.

Calcium Binding and Biodegradation

The log $K_{Ca}$ of RS, SR tetrasodium sulfo CMOS was calculated to be 5.7 with an SC5 of 2.2., while the mixture of 2:1 RS, SR:RR,SS was also 5.7 with an SC5 of 1.7.

The process of this invention for the preparation of the salt of SCMOS includes forming an aqueous mixture of starting reactants containing a sulfo maleate moiety and an alkaline earth metal hydroxide.

The alkaline earth metal hydroxide employed in the reaction mixtures of the inventive process is selected from the group consisting of barium hydroxide, strontium hydroxide or calcium hydroxide. The most preferred alkaline earth metal hydroxide for use in this invention is calcium hydroxide.

The SCMOS salt forming reaction of the present invention is conducted at high concentration in aqueous media about 30% to 40% to afford efficacy and high throughput. The amount of water present may vary and is preferably sufficient to permit the reaction to proceed with the amount of water being about 60% to 70%. The amount may, however, be more or less depending on design parameters.

Desirably, the reactants of the starting mixture for the process are combined in water using physical agitation. In the preferred embodiments of the invention, the alkaline earth metal hydroxide is mixed with an aqueous mixture of the glycolate and sulfo maleate acids, mechanical stirring is employed. The reaction is conducted at atmospheric pressure.

The reaction temperature for the process ranges from about 25° C to about 95° C., preferably from about 25° C. to about 30° C. The reaction temperature is maintained for at least about 1 to 2 hours and preferably no longer than about 5 hours at temperatures ranging preferably from 25° C. to 35° C. The aqueous reaction product typically contains a mixture of SCMOS, sulfomalate and glycolate.

The reaction products obtained by the processes of this invention contain the alkaline earth metal salt of SCMOS. Generally, the work up comprises the steps of filtration to recover the precipitated SCMOS and then washing with water to remove soluble impurities such as calcium glycolate and calcium sulfomalate. Then reduction of the calcium content of the product and acidification or conversion into monovalent cation salts, ammonium salts, morpholinium salts, alkanol ammonium salts and mixtures thereof is accomplished.

The calcium content of the reaction products may be reduced by conventional means. Removal of calcium can be carried out in a number of ways known in the art. In general, simply adding a calcium precipitating material will suffice. Such calcium precipitating materials include alkali metal carbonate, pyrophosphate, sulfates, bicarbonate and/or alkali metal silicate and mixtures thereof, for example, the addition of sodium carbonate will convert the alkaline earth metal salt obtained to the sodium salt. The resulting calcium precipitate can thereafter be removed from the aqueous reaction product mixture by filtration. In an alternative mode, removing calcium from the aqueous reaction product mixtures involves treatment of said mixtures with an appropriate insoluble ion exchange resin or zeolite. No matter what technique is employed, the calcium content of the SCMOS salt prepared by methods herein should desirably be reduced to the extent that calcium is present in an amount of no more than about 1.0% of the SCMOS salt and preferably less than 0.2%, in order to form compositions particularly suitable as detergent builders. This can be accomplished by the method of defensive publication T 101,805.

SCMOS salts formed herein can also be treated, after calcium removal, in a further step, using organic or aqueous solvent extraction to remove excess reactants, such as maleates, or organic reaction by-products, such as fumarates. This can, for example, be accomplished by conventional salt separation procedures using a solvent such as a mixture of methanol and water (4:1 v/v) in which these excess reactants and reaction by-products are relatively soluble and in which the desired SCMOS salt is relatively insoluble as disclosed in U.S. Pat. No. 5,068,420.

At any stage after the SCMOS salt formation, and after reducing the calcium salt content the reaction product can be concentrated by removal of water to the desired extent. Water removal can, for example, after calcium removal, involve substantially complete drying of the reaction product mixture, e.g., by spray drying, so that the SCMOS salt is recovered in solid, e.g., granular, form. The sodium salt of SCMOS in the form of aqueous liquid may be utilized directly in the preparation of detergent compositions or laundry additive products of the types more fully described hereinafter.

It is possible, if desired, to acidify the product mixtures using conventional acidification or ion exchange techniques to convert the SCMOS salts therein to their free acid form. Normally, however, the SCMOS materials of this invention can, after calcium depletion or complete replacement by sodium, be used as builders in their water-soluble salt form, and such acidification is therefore not usually necessary or desirable.

When converted into suitable form, the SCMOS salts can be used as sequestering builders in a wide variety of detergent or laundry additive compositions.

Detergent compositions incorporating the SCMOS salt prepared using the processes of this invention contain as essential components from about 0.5% to about 98% of a surfactant and from about 0.5% to about 99.5% of the SCMOS compounds as a detergency builder, generally in sodium-salt form. Surfactants that are useful in the present invention are the anionic (soap and nonsoap), nonionic zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and Berch, the disclosures of which are incorporated by reference herein. The SCMOS builder can be used either as the sole builder or where desired can be used in conjunction with other well-known builders, examples of which include water-soluble salts of phosphates, pyrophosphates, orthophosphates, polyphosphates, phosphonates, carbonates, polyhydroxysulfonates, polyacetates, carboxylates, polycarboxylates, succinates and the like.

In addition to the surfactant and builder, there may be optionally present additional ingredients which enhance the performance of the detergent composition. Typical examples thereof include the well known soil suspending agents, hydrotropes, corrosion inhibitors, dyes, perfumes fillers, optical brighteners, enzymes, suds boosters, suds depressants, germicides, anti-tarnishing agents, cationic detergents, softeners, bleaches, buffers and the like.

The detergent compositions of the present invention may be in any of the usual physical forms for such compositions, such as powders, beads, flakes, bars, tablets, noodles, liquids, pastes and the like. The detergent compositions are prepared and utilized in the conventional manner. The wash solutions thereof desirably have a pH from about 7 to about 12, preferably from about 9 to about 11.

In addition to their utility as builders in detergent and laundry additive compositions, the SCMOS salts of the invention can, after reducing their calcium content, also be utilized in other contexts wherein water hardness sequestration is required. Other uses are provided in water softening compositions, devices and methods and boiler descaling compositions and methods. It is also theorized that SCMOS can complex heavy metals which react with bleach and thus can stabilize bleach.

It should also be noted that when SCMOS is employed as the free acid or as partly neutralized salt it has utility in metal cleaning composition under pH conditions of about 2 to about 5.

The following examples are designed to illustrate, but not to limit, the practice of the instant invention. All percentages and parts herein are by weight unless indicated otherwise. All ratios herein are mole ratios unless indicated otherwise.

Reaction mixture samples and reaction products were analyzed by NMR. The proton NMR is a 200 MHz Bruker model. Samples are prepared by ion exchanging the calcium salts, followed by neutralization of the acids with sodium carbonate and dissolution in $D_2O$. Peak assignments are as follows:

Sulfomaleic acid 6.4 δ

Sulfomalic acid RS,SR CH 4.3 to 4.38 δCH 3.9 to 3.95 δ

Sulfomalic acid RR, SS CH 4.30 to 4.36 δCH 3.85 to 3.92 δ

The SCMOS peak assignments are in Examples 1 and 2.

Proton magnetic resonance ($^1H$ NMR) were recorded on a Bruker 200 MHz spectrometer or Varian 300 MHz NMR. Proton chemical shifts are reported in parts per million. Samples are prepared by treating the calcium salts with either cation exchange resin, followed by neutralization with sodium carbonate to a pH of at least 9 or by treatment of the calcium salt with sodium carbonate to precipitate out calcium carbonate. Carbon 13 spectra ($^{13}C$ NMR) were recorded on the Bruker at 50 MHz and on the Varian at 75 MHz.

EXAMPLES

EXAMPLE 1

Sulfo maleic anhydride, 2.6 g; 83% active; 0.012 mol, is dissolved in 10 ml water, while maintaining the temperature below 40° C. Glycolic acid (1 g; 0.0135 mol) is added. To this solution is added about 2.0 g (0.026 mol) calcium hydroxide to raise the pH to 11.0. The hazy solution stirred at 25° C. for one hour, during which time a white solid precipitates. The mixture is filtered after two hours. The solid is ion exchange rapidly and neutralized with Na2CO3. $^1H$ NMR and $^{13}C$ NMR show essentially a pair of enantiomers, most probably RS,SR. $^1H$ (200 MHz, $D_2O$): δ3.6–4.0 (dd, 2H), 3.9 (d, 1H), 4.1 (d, 1H) $^{13}C$ NMR (75 MHz, $D_2O$): ppm 68.7 ($\underline{C}H_2O$), 68.9 ($\underline{C}HSO_3$), 78.1 ($\underline{C}HO$)

EXAMPLE 2

Sulfo maleic anhydride, 203 g (85% active); 0.97 mol, is dissolved in 200 ml cold distilled water. Glycolic acid, 73.7 g; 0.97 mol, is added, followed by the slow addition of 167 g (2.2 mol) of calcium hydroxide. pH at this point registers 2.5, so that 24 g (0.3 mol) additional calcium hydroxide was added. Due to the high solids of this solution, an additional 800 ml water. The pH of the hazy solution at this point is 12. During the course of about two hours solid precipitates. After three hours, the mixture is cooled, filtered and redispersed three times in water, 400 ml each time, to remove undesirable by-products or starting material. The flitrate is treated with Amberlite IR-120 cation exchange resin to remove calcium, and the solution is allowed to stand overnight. The solution is decanted and the resin is washed thoroughly until the pH is about 5. The aqueous solution is brought up to pH 8.8 with sodium carbonate and the solution is evaporated to dryness on a roto evaporator then dried in vacuo over $P_2O_5$. Initially the $^1H$ NMR of the entire mixture affords the following: 11.8% sulfo malate, 3% glycolate and 85.2% of a mixture of diastereomers of sulfo CMOS. After purification via the calcium salt, the $^1H$ NMR affords the following 5.5% sulfo malate; 1.2% glycolate; 93.3% of a mixture of diastereoisomers of sulfo CMOS.

$^1H$ and $^{13}C$ both show two diastereoisomers of tetrasodium sulfo CMOS in a ratio of 1.9:1 (RS,SR:RR,SS).

$^1H$ (300 MHz, $D_2O$):

RR,SR isomers δ 3.6–3.95 (dd, 2H), 3.88 (d, 1H), 4.09 (d, 1H)

SS, RR isomers δ3.7–3.90 (dd, 2H), 3.86 (d, 1H), 4.06 (d, 1H)

$^{13}C$ NMR (75 MHz, $D_2O$):

RS,SR isomers ppm 68.71 ($\underline{C}H_2O$), 69.0 ($\underline{C}HSO_3$), 78.1 ($\underline{C}HO$)

RR,SS isomers ppm 68.76 ($\underline{C}H_2O$), 69.3 ($\underline{C}HSO_3$), 79.5 ($\underline{C}HO$)

EXAMPLE 3

Sulfomaleic anhydride 8 g (0.04 mole) is dissolved in 8.5 g of water and agitated 3.2 g (0.04 mole) of glycolic acid is then added to the solution and dissolved. To this solution with continued agitation is added 7.2 g of 50% sodium hydroxide (0.09 mole) and 3.3 g (0.05 mole) of calcium hydroxide. The solution at this stage contains about 50% solute (solids). This solution is agitated for about 5 hours at 25° C. (room temperature) and then dilated to about 10% to 20% by weight solids. The solution is then treated with Amberlite® 1R 104 from Rohm & Haas Co. by mixing the solution with the Amberlite® and agitating until the pH drops to 1 to 1.5. The Amberlite® is then filtered off and the solution is immediately neutralized to pH of 8.6 with sodium carbonate (sodium hydroxide can also be used). The solution was then concentrated by heating and evaporation and dried. The reaction mixture contains 6.16 grams of solid which were analyzed by 200 MHZ N.M.R. as follows:

Sodium sulfo malate 12.5 % wt.

Sodium glycolate 4.4 % wt.

Sodium sulfo (SCMOS) 83.1 % wt.

EXAMPLE 4

An aqueous crutcher slurry containing 46 % by weight of water is spray-dried in a counter-current spray-drying tower to a base powder having a bulk density of 710 g/liter and a moisture content of 15.8%. The formulation of the powder prepared is as follows:

|  | Parts by Weight |
|---|---|
| $C_{12}$–$C_{15}$ alcohol 7EO ethoxylate | 3.0 |
| SCMOS | 23.0 |
| Sodium carbonate | 5.0 |
| Sodium silicate | 6.0 |
| Water and minor components | 10.0 |

A mixture of anionic and nonionic suffactants containing 3.8 parts of $C_{10-13}$ alkylbenzene sulfonic acid and 6 parts of a $C_{12-15}$ primary alcohol 7EO ethoxylate prepared by neutralizing the sulfonic acid with caustic soda solution of 50 % by weight is prepared. This mixture is then heated under vacuum until the water content is reduced to about 3%, resulting in a mole ratio of water to anionic of 1.6. This mixture is then sprayed onto the powder.

A liquid mixture of sodium monostearyl phosphate and petroleum jelly in a weight ratio of 1.3:1 is then sprayed onto the powder at the rate of 0.8 parts to 63 parts.

Finally, the powder is dosed with heat-sensitive components such as oxygen bleaches, perfumes and enzymes in accordance with conventional practice to produce a finished powder having the following composition:

|  | Parts by Weight |
|---|---|
| Sodium $C_{10-13}$ alkylbenzene sulfonate | 4.0 |
| $C_{12-15}$ primary alcohol ethoxylate 7EO | 9.0 |
| SCMOS | 23.0 |
| Sodium carbonate | 5.0 |
| Sodium silicate | 6.0 |
| Sodium sulfate | 26.9 |
| Sodium perborate | 12.0 |
| Sodium carboxymethylcellulose | 0.9 |
| Sodium stearyl phosphate | 0.2 |
| Petroleum jelly | 0.6 |
| Enzyme marumes | 0.4 |
| Cellulose ether anti-redeposition aid | 0.3 |
| Water, perfume, and minor components to | 100.0 |

The finished powder produced will have a bulk density of about 800 g/liter.

It is understood that the examples and embodiments described herein are for illustrative purposes only and that various modification or changes in the light thereof will be suggested to persons skilled in the art and are to be included within the spirit and purview of this application and the scope of the appended claims.

What is claimed is:

1. A process for preparing SCMOS acid comprising:
   (i) reacting
      (a) maleic anhydride with;
      (b) $SO_3$ in a ratio of 1.1 to 1.3 moles of $SO_3$ to 1.0 moles of said maleic anhydride species to form a sulfo malic anhydride mixture;
   maintaining the temperature of said mixture at C. to 80° C. and adding cold water and ice to a temperature of 25° C. to 30° C. to form sulfomaleic acid;
   (iii) adding glycolic acid to said sulfomaleic acid to form an acid mixture;
   (iv) adding an alkaline earth metal hydroxide or a mixture of alkaline earth metal and alkali metal hydroxides to a pH of about 11 and at a temperature of about 25° C to 50° C. to form sulfocarboxymethyloxy succinic acid (SCMOS) alkaline earth metal salts;
   (v) precipitating out said salts and recovering said salts as the pH drops to 10.2–10.5;
   (vi) washing said salts with water to solubilize impurities; and
   (vii) converting said salts to sodium salts by the use of a material selected from the group consisting of ion exchange resin, sodium carbonate and mixtures thereof.

2. A process as defined in claim 1 wherein the reaction is extended for a period of about 5 hours at a temperature of less than 60° C.

3. A process as defined in claim 1 wherein the alkaline earth metal hydroxide is calcium hydroxide.

4. A process as defined in claim 1 wherein the mixture of alkaline earth metal hydroxide and alkali metal hydroxide is $Ca(OH)_2$ and NaOH.

5. A process as defined in claim 1 wherein the mole ratio of said a) to said b) is 1.2 to 1.

6. A process as defined in claim 1 wherein the SCMOS acid is recovered from the reaction mixture.

7. A method for purifying the product obtained from claim 1 by contacting the sodium salts from step (vii) with a mixed methanol/water solvent after reducing the calcium content of the product.

8. A process as defined in claim 1 wherein the step (iv) is carried out at a temperature of 25° C. to 35° C.

* * * * *